US 7,490,924 B2

(12) United States Patent
Haluzak et al.

(10) Patent No.: US 7,490,924 B2
(45) Date of Patent: Feb. 17, 2009

(54) DROP GENERATOR FOR ULTRA-SMALL DROPLETS

(75) Inventors: Charles C Haluzak, Corvallis, OR (US); Kenneth E. Trueba, Philomath, OR (US); Terry E McMahon, Albany, OR (US); Donald W Schulte, Corvallis, OR (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 257 days.

(21) Appl. No.: 11/479,770

(22) Filed: Jun. 30, 2006

(65) Prior Publication Data
US 2006/0243387 A1    Nov. 2, 2006

Related U.S. Application Data

(60) Division of application No. 10/412,544, filed on Apr. 11, 2003, now Pat. No. 7,125,731, which is a continuation-in-part of application No. 10/003,780, filed on Oct. 31, 2001, now Pat. No. 6,627,467, and a continuation-in-part of application No. 10/000,425, filed on Oct. 31, 2001, now Pat. No. 6,698,868.

(51) Int. Cl.
B41J 2/05 (2006.01)
(52) U.S. Cl. ............................... 347/63; 347/65
(58) Field of Classification Search ............ 347/20, 347/44, 45, 47, 56, 61, 63, 65, 107
See application file for complete search history.

(56) References Cited

U.S. PATENT DOCUMENTS

| 3,852,563 | A | | 12/1974 | Bohorquez et al. | 347/204 |
| 4,438,191 | A | | 3/1984 | Cloutier et al. | 430/324 |
| 4,809,428 | A | | 3/1989 | Aden et al. | 29/611 |
| 4,847,630 | A | | 7/1989 | Bhaskar et al. | 347/63 |
| 4,851,371 | A | | 7/1989 | Fisher et al. | 438/21 |
| 4,875,968 | A | | 10/1989 | O'Neill et al. | 216/27 |
| 4,894,664 | A | | 1/1990 | Tsung Pan | 347/63 |
| 5,041,190 | A | | 8/1991 | Drake et al. | 438/21 |
| 5,160,577 | A | | 11/1992 | Deshpanda | 216/27 |
| 5,194,877 | A | | 3/1993 | Lam et al. | 347/63 |
| 5,211,806 | A | * | 5/1993 | Wong et al. | 216/27 |
| 5,306,370 | A | | 4/1994 | Herko et al. | 156/155 |
| 5,308,442 | A | | 5/1994 | Taub et al. | 216/27 |
| 5,317,346 | A | | 5/1994 | Garcia | 347/63 |
| 5,350,616 | A | * | 9/1994 | Pan et al. | 347/63 |
| 5,478,606 | A | | 12/1995 | Ohkuma | 427/555 |

(Continued)

FOREIGN PATENT DOCUMENTS

DE    19536429    4/1997

(Continued)

OTHER PUBLICATIONS

Jul. 16, 2004 International Search Report and Written Opinion; ISO:EPO; Corresponding app. No. PCT/US/2004/010974; 11 pages.

(Continued)

Primary Examiner—Juanita D Stephens

(57) ABSTRACT

A drop generator includes a substrate, and a mandrel that is disposed on the substrate for shaping the drop generator chamber. The mandrel is covered by the orifice member and thereafter removed.

16 Claims, 4 Drawing Sheets

U.S. PATENT DOCUMENTS

| | | | |
|---|---|---|---|
| 5,851,412 A | 12/1998 | Kubby | 216/27 |
| 5,894,841 A | 4/1999 | Voges | 128/203.12 |
| 6,036,874 A | 3/2000 | Farnamm | 216/27 |
| 6,113,221 A | 9/2000 | Weber | 347/61 |
| 6,137,443 A * | 10/2000 | Beatty et al. | 347/63 |
| 6,153,114 A | 11/2000 | Figueredo et al. | 216/27 |
| 6,204,182 B1 | 3/2001 | Truninger et al. | 438/691 |
| 6,627,467 B2 | 9/2003 | Haluzak et al. | 438/21 |
| 6,698,868 B2 * | 3/2004 | Trueba et al. | 347/63 |
| 2003/0081072 A1 | 5/2003 | Trueba | 347/63 |
| 2003/0082841 A1 | 5/2003 | Haluzak | 438/21 |

FOREIGN PATENT DOCUMENTS

| | | |
|---|---|---|
| EP | 0244214 | 4/1997 |
| EP | 0783970 | 7/1997 |
| EP | 0814380 | 12/1997 |
| EP | 122938 | 7/2002 |
| JP | 5995156 | 10/1984 |
| JP | 0610098557 | 5/1986 |
| JP | 62094347 | 4/1987 |
| JP | 0040052144 | 2/1992 |

OTHER PUBLICATIONS

U.S. Appl. No. 09/556,035, filed Apr. 20, 2000, Droplet Plate Architecture in Ink-Jet Printheads.

* cited by examiner

DROP GENERATOR FOR ULTRA-SMALL DROPLETS

CROSS-REFERENCE TO RELATED APPLICATION

This application is a divisional of U.S. utility application entitled, "Drop Generator for Ultra-Small Droplets," having Ser. No. 10/412,544, now U.S. Pat. No. 7,125,731, filed Apr. 11, 2003, which is a continuation-in-part of U.S. patent application Ser. Nos. 10/003,780, now U.S. Pat. No. 6,627,467, filed Oct. 31, 2001, entitled "Fluid Ejection Device Fabrication", and 10/000,425, now U.S. Pat. No. 6,698,868, filed Oct. 31, 2001, entitled "Thermal Drop Generator for Ultra-Small Droplets", each of which is entirely incorporated herein by reference.

BACKGROUND OF THE INVENTION

The ongoing advances in medicine and biotechnology are providing many effective and promising systemic therapies that call for the delivery of biological and chemical substances (such as peptides, proteins, and small molecules) to a patient's bloodstream. There are various problems associated with getting certain substances to the bloodstream by conventional delivery means, such as transdermal and oral. For instance, oral delivery of therapeutic proteins does not work because the proteins are digested before they have an opportunity to reach the bloodstream. Thus, for this and other reasons, it is best to deliver such substances to the bloodstream by as direct a route as possible.

An aerosol is a gaseous suspension of very fine solid or liquid particles. Aerosols are presently used for delivering certain drugs to a patient's lungs. Delivery of drugs or other therapeutic substances to a patient's lungs is sometimes referred to as pulmonary delivery.

The innermost tissue of the lung is known as the alveolar epithelium, which comprises hundreds of millions of tiny air sacs, called alveoli, that are surrounded by a large network of blood capillaries. The alveoli enable rapid absorption of fluids from the alveoli to the bloodstream. Most effective pulmonary delivery is accomplished when the substance is delivered to the alveoli. The delivery process requires the generation of very small particles or droplets that can be entrained in a gas as an aerosol and inhaled by the patient into the alveoli for transfer to the bloodstream.

The lung's alveoli can readily absorb fluid droplets having diameters equal to or less than about 4 µm, which represents a volume of about 33 femtoliters. A femtoliter is one quadrillionth ($10^{-15}$) of a liter. Larger drops tend to contact the lung walls before reaching the alveoli and are less likely to permeate the wall to the bloodstream because the airway to the alveoli is lined with a thick, ciliated mucus-covered cell layer.

A popular pulmonary delivery mechanism is known as a metered dose inhaler (MDI). These are widely used for the delivery of asthma medication. While an MDI delivery system may be effective for medications designed to medicate the lung tissue, they are not optimal for delivery of substances to the alveoli (hence, to the bloodstream). In this regard, an MDI typically combines the drug with a propellant in a pressurized container. Actuation of the device releases metered doses of the aerosol, but the droplet size distribution is large, and the vapor pressure of the propellant varies with temperature and number of uses. Thus, the behavior of the material in the air stream and the extent to which droplets reach the alveoli becomes somewhat unpredictable.

In view of the foregoing, it can be appreciated that there is a desire for a droplet generator that can reliably produce ultra-small-volume droplets with a generally uniform size distribution for entrainment in aerosols.

SUMMARY OF THE INVENTION

The present invention is directed to a drop generator. The drop generator includes a substrate and a mandrel that is disposed on the substrate for shaping the drop generator chamber. The mandrel is covered by the orifice member and thereafter removed.

Methods and apparatus for carrying out the invention are described in detail below. Other advantages and features of the present invention will become clear upon review of the following portions of this specification and the drawings.

DETAILED DESCRIPTION

Figure 1:
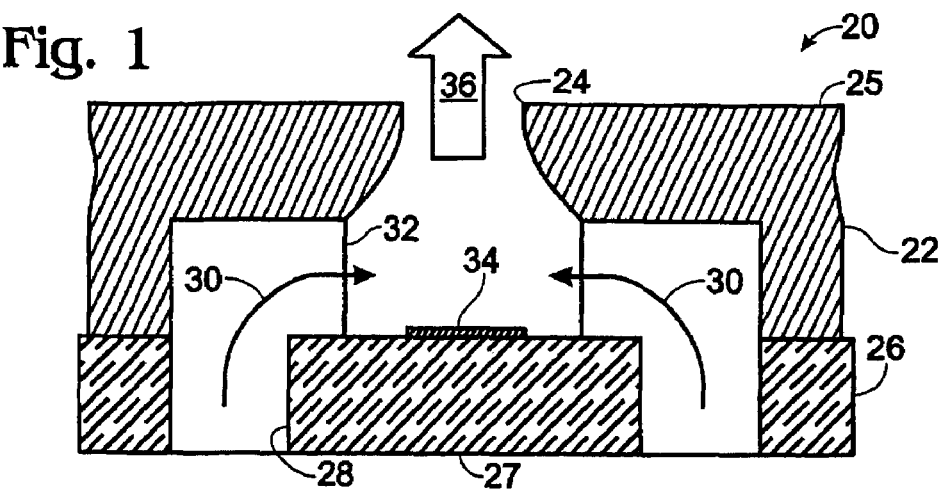
FIG. 1 is a schematic representation of a drop generator configured in accordance with one embodiment of the present invention.

FIG. 1 is a schematic representation of a drop generator that is formed in accordance with one aspect of the present invention. In that figure, the drop generator 20 is depicted in cross section. A solid orifice structure 22 is constructed as a generally planar member having a circular orifice 24 defined in it. The orifice 24 has a minimum diameter of about 2 micrometers (µm) at the surface 25 of the orifice structure 22. The orifice diameter gradually increases in the inward direction as shown in FIG. 1. The orifice shape need not be restricted to being circular (as viewed in plan). Other near-circular shapes will suffice and are contemplated, typically with the minimum diametric dimension of the orifice being 2 µm across.

The orifice structure 22 is continuous with one side of a solid substrate member 26 that underlies the orifice structure. The opposing side 27 of the substrate member 26 is in communication with a fluid. Two inlets 28 are defined in the substrate to allow the fluid to flow (as depicted by arrows 30)

into a chamber 32. The chamber 32 is a small reservoir for holding liquid prior to ejection of the fluid from the chamber through the orifice 24.

The mechanism for ejecting the fluid from the chamber is the generation of a vapor bubble in the chamber by a heat transducer 34 that is inside the fluid-filled chamber. The rapid expansion of the bubble ejects or "fires" the fluid as a droplet. For computational purposes the heat transducer 34 is considered a planar member (such as a thin-film resistor) that, upon actuation, provides an energy density of about $0.014\ \mu J/\mu m^2$. In some embodiments, the fluid under consideration may be a liquid that has a viscosity of about 3 cp and a boiling point of 100° C.

In accordance with the present invention, a droplet having a volume in the range of 10 femtoliters is ejected from the chamber, along a trajectory as shown by arrow 36, upon activation of the heat transducer 34. Such droplets, being less than 100 femtoliters, are characterized here as ultra-small droplets. In one implementation of this invention, the volume of the chamber for producing the ultra-small droplets is only slightly larger than the droplets themselves. The fabrication of such drop generators having ultra-small chamber volumes must be carefully controlled to ensure that the generators can be reliably reproduced. This is especially important with respect to maintaining the shape and size of the chamber during fabrication of the drop generator. What follows is a description of one approach to fabricating drop generators in accordance with the present invention.

Figure 6:
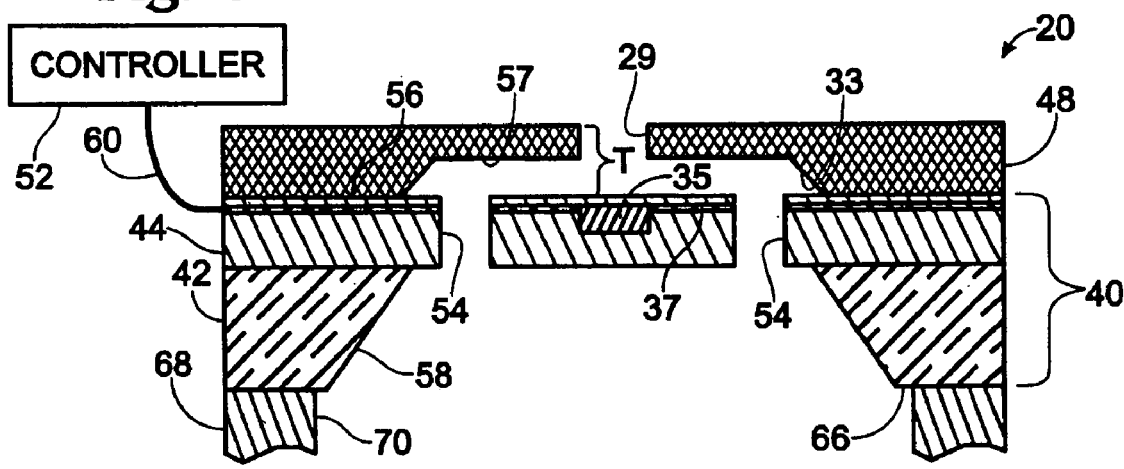
FIG. 6 is an enlarged cross section illustrating one completed drop generator embodiment.

FIG. 6 shows a greatly enlarged cross section of an embodiment of a drop generator 20 formed in accordance with the present invention. For illustrative purposes, a single drop generator is shown but, as will become clear, the fabrication process allows the simultaneous production of multiple drop generators. The number of drop generators produced depends upon the amount of droplets that are required for a given application. One can consider this requirement in terms of flux, or the number of droplets that are simultaneously ejected from the drop generators. For greater flux requirements, more drop generators can be fabricated. For example, an array of 9000 drop generators operating at 200 kHz could be employed for producing droplets at a volumetric rate of about 25 microliters per second.

The exemplary drop generator 20 includes a rigid substrate 40 that can be a silicon base 42, which may be a single-crystal silicon wafer upon which has been grown an insulation layer, such as silicon dioxide. The substrate 40 may be as described in the prior art relating to ink-jet printing, an example of such art being U.S. Pat. No. 4,719,477. The substrate may be made of silicon, glass, gallium arsenide, silicon on sapphire (SOS), epitaxial formations, germanium, germanium silicon, diamond, silicon on insulator (SOI) material, selective implantation of oxygen (SIMOX) substrates, or similar substrate materials.

The substrate includes a layer of resistive material, such as tantalum-aluminum portions 35. The resistive material may alternatively be tantalum nitride, hafnium boride, or tungsten silicon nitride. The resistive portions 35 are individually connected to thin conductors 37 that are patterned from a conductive layer. These conductors 37, which can be aluminum or an aluminum alloy, are connected to traces on a flex circuit 60 (shown diagrammatically in FIG. 6). That circuit connects with a controller 52 for operating the drop generators as described more fully below.

The substrate 40 may incorporate CMOS circuit components for permitting the use of multiplexed control signals for firing the drop generators. This simplifies the connection with the heat transducers 35 (that is, eliminates the need for numerous traces directly connected with the heat transducers). Also, the complex control logic afforded by the CMOS circuitry enables, for example, precise metering requirements to be programmed into that circuit and, thus, carried with a device (such as an inhaler) for which the drop generators are fabricated. For instance, if medicinal fluid droplets are to be ejected for an aerosol treatment that requires gradually increasing dosage, the control circuitry can be programmed to fire additional drop generators (increase the flux) with each subsequent use of the device.

The individual portions 35 of the resistive layer (FIG. 6), hereafter referred to as heat transducers or resistors, the associated conductors 37, and CMOS circuit components are part of what may be collectively referred to as the control layer 44 of the substrate 40, which also includes the insulating layer of silicon dioxide, a resistor-protective passivation (typically composed of silicon nitride ($Si_3N_4$) and silicon carbide (SiC)), and other sub-layers (such as a cavitation-protection layer that can be composed of a refractory metal such as tantalum or a tantalum-aluminum alloy) as described in detail, for example, in U.S. Pat. No. 4,719,477.

The requirement for a passivation layer may be minimal in instances where the fluid to be ejected from the chamber is not damaging to the resistor. In any event, the present invention may be incorporated with any of a number of planar transducer configurations.

With continued reference to the completed drop generator illustrated in FIG. 6, a unitary orifice member 48 is affixed to the control layer 44 and is shaped to define for each drop generator an orifice 29 and underlying fluid chamber 33 that is continuous with the orifice. The transducer 35 is selectively driven (heated) with a pulse of electrical current delivered via the conductors 37. (The conductors bypass the hereafter-described inlets 54.) The heat from the transducer is sufficient to vaporize some of the liquid in the chamber 33, thereby forcing the fluid through the orifice 29 in the form of a droplet as described above with respect to FIG. 1.

It is contemplated that other mechanisms for ejecting the fluid may be employed, such as a piezoelectric transducer. Also, several different cross sectional shapes of orifices are contemplated. For example, a shape known as non-reentrant may be employed. This shape features an orifice diameter that generally increases in the direction of the droplet expulsion from the chamber.

Each chamber 33 is refilled after each ejection with fluid that flows into the chamber through inlets 54 that are formed through the control layer 44. In one embodiment, the upper surface 56 of the control layer 44 of the substrate is patterned and etched to form the inlets 54 before the orifice member 48 is attached to the substrate, and before a channel 58 is etched in the base 42 of the substrate 40, as described below. (The surface 56 is named "upper" for convenience and with the understanding that the surface 56 may be oriented beneath the remainder of the control layer 44 when the drop generator is inverted from the orientation shown in FIG. 6.)

Figure 2:
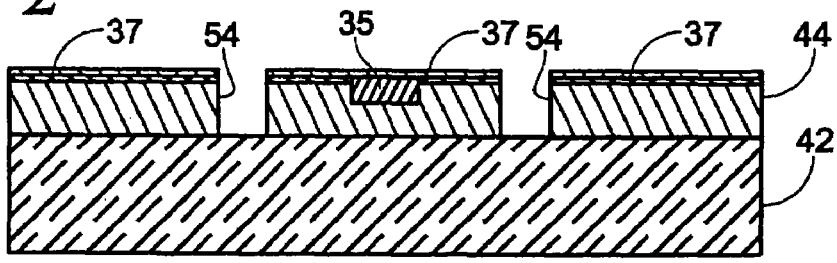
FIG. 2 is an enlarged cross sectional diagram of one step of fabricating a representative drop generator in accordance with one embodiment of the present invention and illustrating a substrate and applied control layer.

The particulars of the fabrication steps of the drop generator 20 are described with reference first to FIG. 2. Shown there is substrate base 42 after it has been processed to carry the control layer 44 that includes the previously formed inlets 54.

Figure 3:
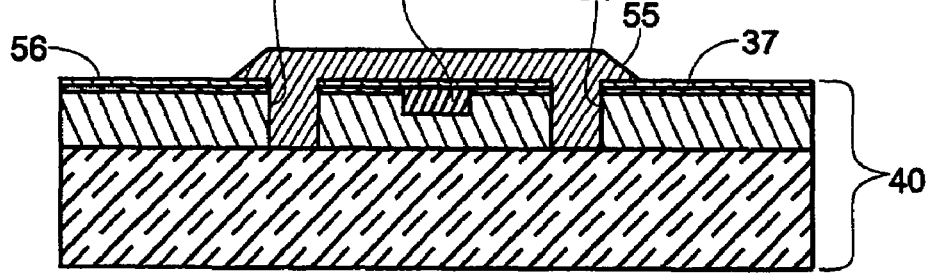
FIG. 3 illustrates a step following that of FIG. 2 including the formation of a removable mandrel.

FIG. 3 illustrates the substrate 40 after formation of a removable mandrel 55 that temporarily fills the inlets 54 and is shaped to define the final shape of the chamber 33 as shown in FIG. 6. As will be described, the ultra-small chamber volume is defined in part with a photopolymer material that is exposed to form the orifice member 48 (FIG. 6). The use of a mandrel, such as depicted at 55 in FIG. 3, helps to ensure that the resulting orifice member will be a substantially planar member having a predictable thickness "T" (FIG. 6), which ensures that the correct chamber volume is in place for the desired ultra-small-volume drop generator.

Put another way, in the absence of the use of a mandrel in accordance with the present invention, the normal erosion and slight deformation of photopolymer material that occurs in the course of exposing portions of that material (which erosion may not affect larger-scale drop generator fabrications) will result in unacceptably larger orifices and smaller chambers than desired when ultra-small chamber volumes are sought. That is, in working with ultra-small chamber volumes, the photopolymer fabrication approach does not provide the fabrication tolerances required for such small chambers. The use of the mandrel of the present invention supports the complete exposure and cross-linking of the photopolymer material in a manner that reduces erosion and deformation of that material during processing of the orifice member, thereby providing a more predictable final chamber and orifice size.

As will become clear upon reading this description, in one sense the use of a removable mandrel 55 is akin to a lost-wax method of casting whereby replaceable material, wax, is used to support and define the shape of an outer structure (such as a mold) that is built around the wax. The wax is removed once the mold is complete.

In one embodiment the mandrel is comprised of spin-on glass (SOG) material, which can be a mixture of silicon dioxide suspended in a solvent solution with dopants such as boron or phosphorous. Alternatively, the SOG may be a siloxane-type, which is a SiO polymer with attached methyl groups.

The SOG-type mandrel is applied using spin coating techniques. The mandrel material fills the inlets 54 and builds to a thickness that matches the height of the chamber 33 between the upper surface 56 of the control layer 44 and what will become the underside 57 of the orifice member 48 at the orifice 29 (FIG. 6).

The SOG is thereafter patterned to define the chamber shape and portions outside of that shape are etched away using, for example, HF, to leave the mandrel 55 configuration illustrated in FIG. 3. The SOG material helps to maintain the planarity of the surfaces of the later-applied and processed orifice member 48. Also, the SOG material is advantageous because it adheres well to the orifice member material, which is described below.

In an alternative embodiment the mandrel could be made from metal, such as aluminum, applied and shaped using metal deposition and etching (wet or dry) techniques. Planarization of the metal mandrel may be needed, and this can be accomplished using mechanical, resist etch-back, or chemical-mechanical processes (CMP). The use of a polysilicon mandrel is also contemplated.

Figure 4:
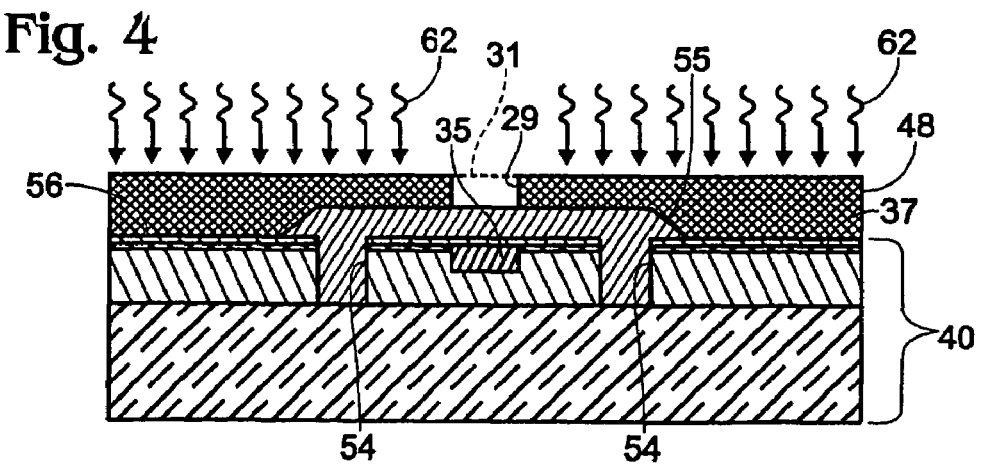
FIG. 4 illustrates a step following that of FIG. 3 including the application and exposure of orifice member material.

With the removable mandrel in place, the orifice member 48 is applied to the upper surface 56 of the substrate, across the area of the mandrel 55 (FIG. 4). In one embodiment, the orifice member is a slow-cross-linking polymer. The slow cross-linking polymer is made by mixing optical dye (such as orange #3, ~2% weight) into either a photoimagable polyimide or photoimagable epoxy transparent polymer material. By adding dye, the amount of electromagnetic energy required is greater than non-dye mixed material to cross-link the material.

The polymer is applied using a spin-coating tool, such as one manufactured by Karl Suss, KG. In one embodiment, the photoresist material comprises a photo-polymerizable epoxy resin known generally in the trade as SU-8. Examples of such materials are available from MicroChem Corp. of Newton, Mass. and sold under the name of SU8-5 and SU8-10. It will be appreciated, however, that the orifice member could comprise any of a number of photoresist materials that become insoluble in developing solutions after exposure to electromagnetic radiation, such as UV radiation.

Alternatively, the orifice member can be composed of a stress-graded dielectric such as silicon dioxide, variable in its composition (stress) throughout the thickness thereof, and may be planarized by processes, if desired, to improve flatness of the top surface thereof.

The spin-coating process associated with the spin-coating tool allows a planar surface to be formed as the slow-cross-linking polymer covers the mandrel 55. An exemplary process for spin coating is to spread a layer of the resist onto a substrate wafer (which carries a plurality of mandrels for forming an associated plurality of drop generators) with the spin coating tool set to 70 rpm with an acceleration of 100 rpm/s and a spread time of 20 seconds. The spinning is then stopped with a deceleration of 100 rpm/s and rest for 10 secs. The coated substrate is then spun at 1060 rpm at an acceleration rate of 300 rpm/s for 30 secs to spread the resist over the entire substrate.

Alternative polymer application processes can be used, including roll coating, curtain coating, extrusion coating, spray coating, dip coating, and electrophoretic deposition.

FIG. 4 illustrates the exposure of the layer of the cross-linking polymer material of member 48 with a high dosage of electromagnetic energy (illustrated with arrows 62). In an exemplary embodiment, this step is carried out with a Micralign scanning projection aligner as manufactured by SVG of San Jose, Calif., with an exposure setting that is sufficient to expose and cross link the entire depth of the orifice member polymer.

The energy (such as UV radiation) is applied to the orifice member material through a mask (not shown). The mask is a device comprising, for example, a quartz substrate patterned with opaque material such as chromium to define (by leaving unexposed) the shape of the orifice 29. The unexposed portion of the polymer that represents the orifice 29 (shown at dashed line 31 in FIG. 4) is then removed using, for example, a developing-tool process comprising a 70-second development in N-methyl-2-pyrrolidinone (NMP) at 1 krpm and an 8 second mix of isopropyl alcohol (IPA) and NMP at 1 krpm, then a 10-second rinse with IPA at 1 krpm, and, finally, a 60 second spin at 2 krpm. Such a developing tool is available from Solitec Wafer Processing, Inc., of San Jose, Calif.

Figure 5:
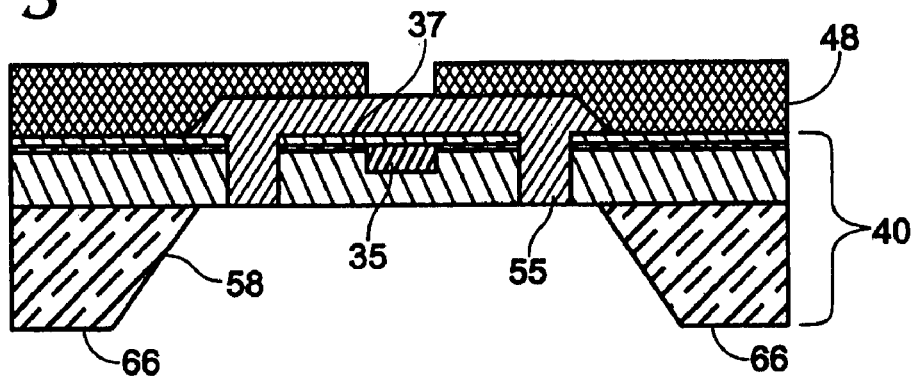
FIG. 5 illustrates a step following that of FIG. 4, including etching of the underside of the substrate.

FIG. 5 shows the drop generator upon the completion of the orifice member development step. The underside 66 of the substrate is then etched with a silicon etch, such as tetramethyl ammonium hydroxide (TMAH) to create the channel 58. The channel 58 is intended for fluid communication with the inlets 54 as explained below.

At the time or subsequent to the creation of the channel 58 in the substrate base 42, the mandrel 55 is removed. In the embodiment using the SOG material, an HF etch can be carried out on both sides of the substrate for removing the mandrel to arrive at the configuration shown in FIG. 6. Other mandrel materials would require suitable etchants for removing the mandrel. For example, a standard wet etch (phosphoric acid, nitric acid, acetic acid, wetting agent and water) may be used as etchants in instances where aluminum is used as a mandrel, or sulfuric peroxide and/or sodium hydroxide may be used. TMAH may be used when a polysilicon mandrel is employed.

In one embodiment, the height of the chamber 33 (that is, between the top surface 56 of the control layer and the underside 57 of the orifice member covering the chamber) is selected to be about 2 μm. Any of a number of chamber shapes (rounded or rectilinear walls) will suffice. In one embodiment, the overall chamber volume is about 25 femtoliters. This volume can be considered as the volumetric portion of the chamber over the transducer 35 as well as the volume of the orifice 29. A chamber of this overall volume, and an associated transducer having an area of about 9 $\mu m^2$, will produce a droplet having a volume in the range of 10 femtoliters. Of course, one of ordinary skill in the art will understand that the viscosity of the fluid and other factors will affect droplet volume. The foregoing dimensions relate to a liquid having a viscosity of about 3 cp and a boiling point of 100° C.

A supply of fluid may be provided to the substrate channel 58 in any of a number of ways. For example, the substrate undersurface 66 may be attached to the outer surface of a body 68 of a device (FIG. 6) that carries a reservoir of liquid. The body surface is configured with several conduits 70 (one of which is shown in FIG. 6), each conduit 70 aligning with a channel 58 for directing the liquid from a reservoir to the channel. As noted above, a substrate can carry many drop generators 20, several of which can be fluidically coupled to the linear channel 58 in the substrate, and the substrate can carry several of such channels.

Figure 7:
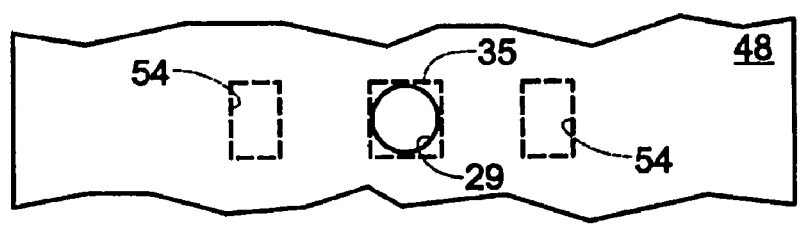
FIG. 7 is a top plan view of the embodiment shown in FIG. 6.

FIG. 7, shows in a top plan diagram the arrangement of the exemplary orifice 29, transducer 35, and inlets 54 of the embodiment of FIG. 6. There, liquid flows from the channel 58 (FIG. 6) into two inlets 54 disposed on opposite sides of the transducer 35. It may be desirable to alter this arrangement so that only a single inlet 54 is provided on one side of the transducer.

Figure 8:
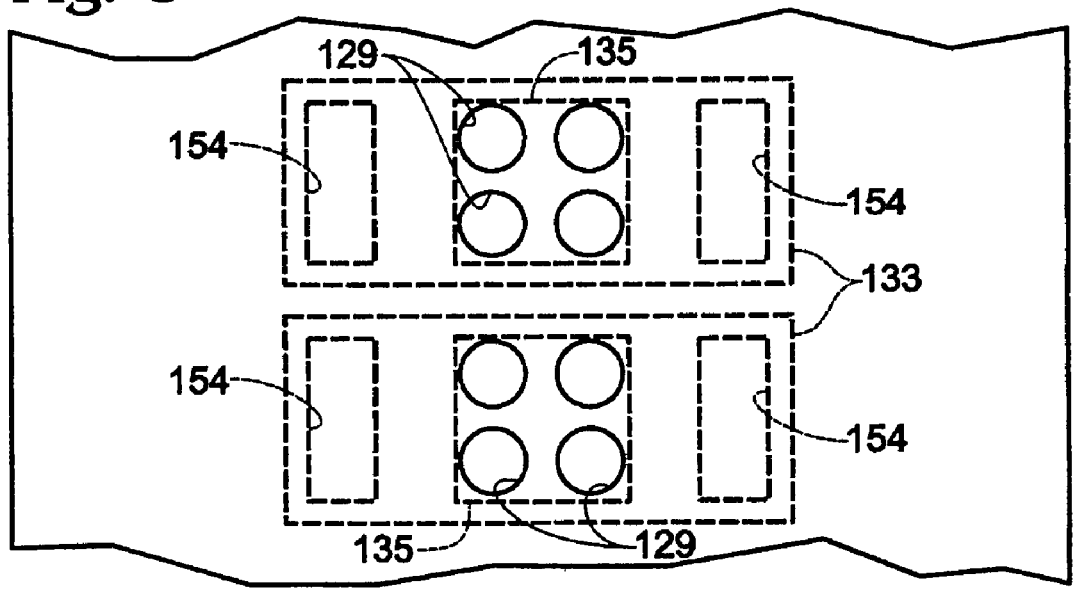
FIG. 8 is a top plan view showing an alternative embodiment of the invention.

FIG. 8 shows in a top plan diagram an alternative arrangement of orifice, resistor, and inlet components of an exemplary pair of chambers 133 as formed in accordance with the present invention. Here, the orifice member is formed with four orifices 129 overlying the four corner portions of the transducer 135. The fluid provided to the transducer 135 flows through a pair of inlets 154, one inlet on each side of the transducer 135.

Figure 9:
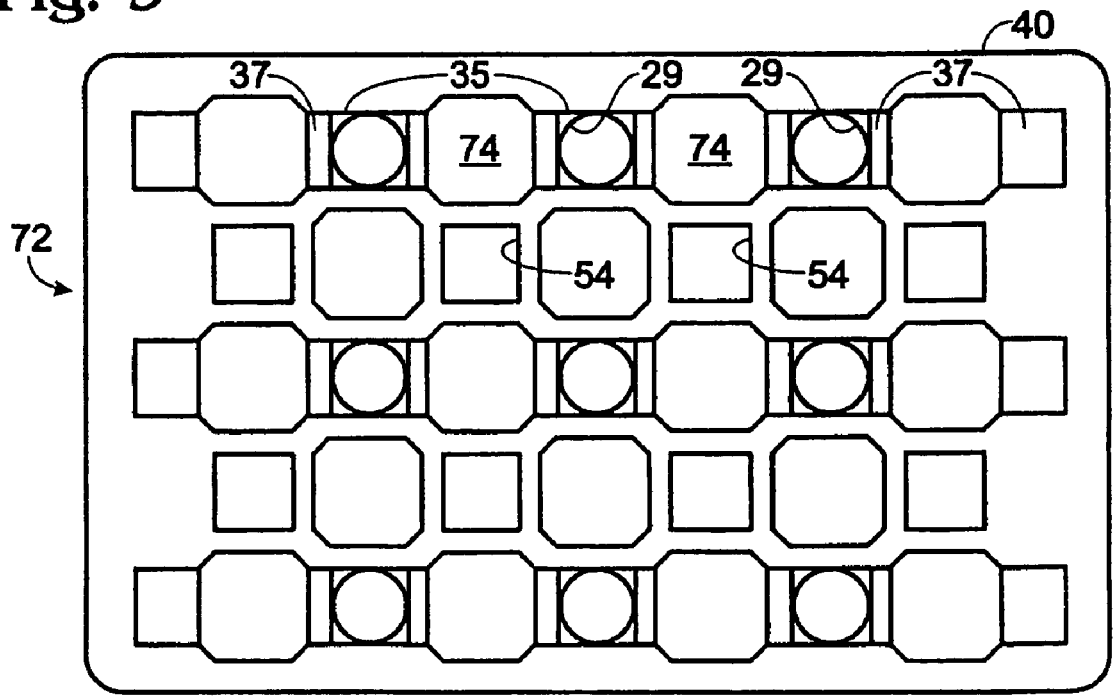
FIG. 9 is a diagram illustrating one arrangement of an array of drop generators formed in accordance with an embodiment of the present invention.
Figure 10:
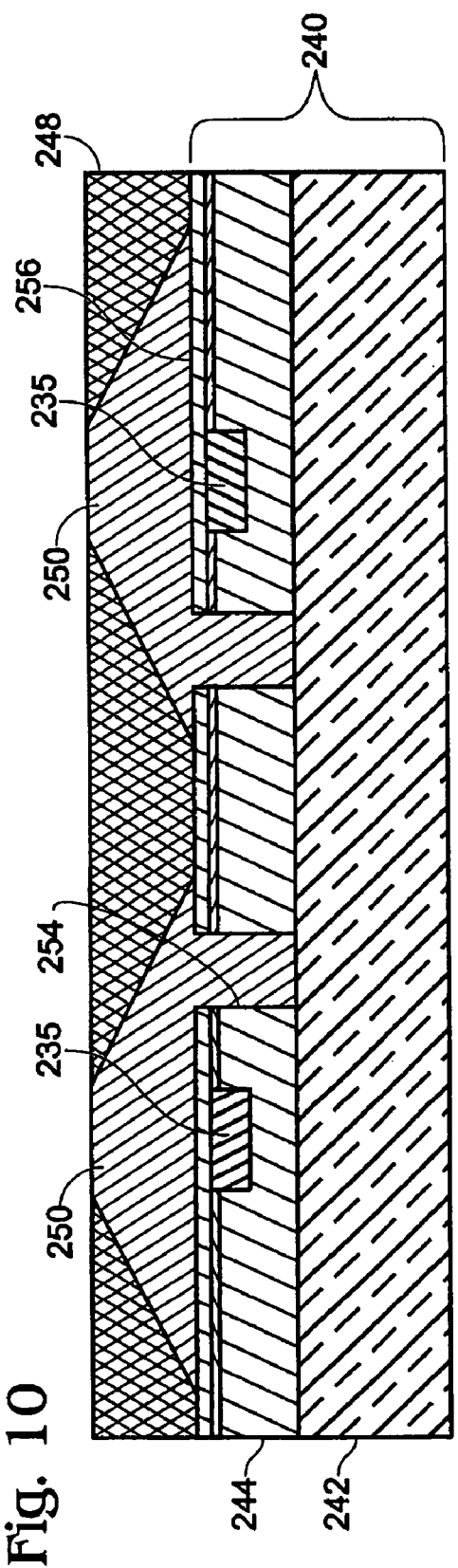
FIG. 10 is an enlarged cross sectional view illustrating a step in the process of fabricating a drop generator in accordance with an embodiment of the present invention.

FIG. 9 is a diagram for illustrating yet another one of several ways of arranging a small group of drop generators on a substrate 40 (the drop generators being made in a batch following the process steps set forth above). This overall device (substrate with multiple drop generators) can be considered a drop generator head 72. The diagram of FIG. 9 is a plan view showing some of the drop generators, and wherein the circular items represent the array of orifices 29 that are above the transducers 35. The transducers 35 are connected by the conductive layers 37 that extend to a location near the edges of the substrate 40 for connection with the above-mentioned circuit 60 that leads from the controller.

In the embodiment of FIG. 9, the orifice member 48 is formed to extend between the upper surface 56 of the control layer 44 (see FIG. 6) in the regions away from the orifices, thereby to define barrier islands 74 as shown in FIG. 9 for supporting the orifice member on the control layer 44. Thus, the chambers of this drop generator head 72 are generally contiguous with one another. Also, in this embodiment, the inlets 54 are square in cross section and arranged so that there are up to four inlets 54 adjacent to each transducer 35.

Other arrangements are contemplated. For example, the transducers and orifices need not be aligned in a 90-degree grid as shown in FIG. 9. Rather, the transducers and orifices can be arranged in staggered columns and/or rows.

As mentioned above, the present invention provides a drop generator for creating fluid droplets having volumes in the range of tens of femtoliters that, for example, are suitable for entrainment in an aerosol for effective pulmonary delivery. For instance, the drop generator head 72 may be mounted to receive a medicinal liquid (or any liquid-based biological and chemical substances as mentioned above).

Having here described preferred embodiments of the present invention, it is anticipated that individuals skilled in the art may make other modifications thereto within the scope of the invention. For example, the mandrel material may be selected to be heavily dyed (as compared to the orifice member material) photo-polymerizable epoxy such that exposure to the radiation that cross-links the orifice member will not do the same to the mandrel material. That is, in such an embodiment, the mandrel material is a relatively slower-cross-linking polymer as compared to the orifice member material. Thus the polymer mandrel can be dissolved for removing the mandrel after the orifice material is completely formed.

In one embodiment, the mandrel material and orifice member material are selected to provide a wetting characteristic of the orifice member material such that it wets (i.e., has a contact angle of less than 90 degrees) the surface of the mandrel to which it is applied. This wetting characteristic ensures that the interface between the removable mandrel and the orifice member is continuous and free from air bubbles and other irregularities that may occur if the orifice member material was non-wetting as respects the mandrel. Moreover, the mandrel material may be selected (or surface treated) so that after that material is removed from the chamber 33 there remains a residue on the chamber surface that enhances the wetting characteristic of the chamber surface. This will improve fluid flow into and out of the chamber and reduce the likelihood of entrapping air in the chamber.

It is also contemplated that the mandrel material may be shaped to include the cylindrical (or otherwise shaped) portion that defines each orifice (as shown at dashed line 31 in FIG. 4), so that the orifice material, such as the described SU-8 or any other suitable orifice material, may be spun-on and exposed without the need to pattern separately the individual orifice portions. In this case, the use of a chemical-mechanical polishing (CMP) step would be required for planarizing the orifice material surface and ensuring no orifice material overlies the cylindrical portion 31 before the next process step (removal of the mandrel material) is undertaken. One such embodiment is discussed next with reference to FIGS. 10 and 11.

In the embodiment of FIG. 10, mandrel material is deposited over the substrate 240 to fill a pair of inlets 254. The mandrel or sacrificial material is then patterned to form mandrel bumps 250, a pair of which is shown in the figures. As can be seen in FIG. 10, the two bumps 250 are each located to cover an inlet 254 and a transducer 235, although more than one inlet per chamber could be formed. In this embodiment (FIGS. 10 and 11), adjacent inlets 254 are near enough for receiving fluid from a common channel 258 that is formed as described below in connection with FIG. 11.

FIG. 10 also illustrates the result of a deposition of another layer over the bumps 250. That layer, provided as by silicon dioxide deposition, will serve as the orifice member 248. The deposition may be plasma enhanced chemical vapor deposition (PECVD) having a thickness in a range from about 1 μm to about 20 μm, and will situate layer 248 over the bumps 250 and, away from the bumps, upon upper surface 256 of the control layer 244.

The orifice material 248 is then planarized, such as by etch-back or chemical mechanical planarization (CMP), so as to expose upper portions of the pair of bumps 250, as is shown in FIG. 10. CMP produces accuracy of the resultant thickness of layer 248 of about plus or minus 800 angstroms.

The planarization process thus defines at each bump 250 an orifice 229. In this embodiment, the surface 231 that defines the chamber 233 and orifice 229 has a constant slope between the orifice 229 and the upper surface 256 of the orifice member 248. That is, the location on the chamber wall where the chamber ends and the orifice begins cannot be discerned.

Figure 11:
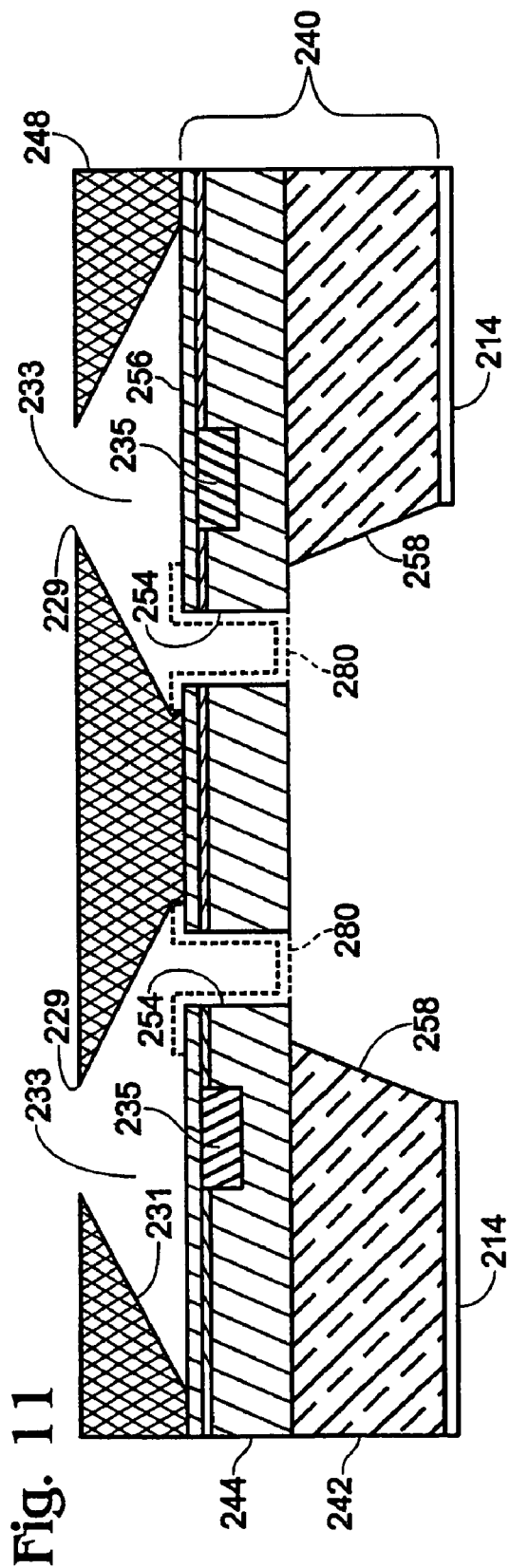
FIG. 11 is an enlarged cross section illustrating the completed drop generator embodiment of FIG. 10.

A selective etch process is then used to remove the bumps 250. The result of the removal of the bumps 250 is seen in FIG. 11. The removed bump material defines the chambers 233 that receive fluid from inlets 254, as well as the orifices 229.

In this, as well as the previously discussed embodiments, a protective layer may be applied to line the inlets 254 and cover part of the upper surface 256 of the substrate that is in the vicinity of the inlets 254. This layer is applied before the mandrel bumps 250 are deposited. This protective layer, as shown in dashed lines 280 in FIG. 11, will have a generally U-shape in cross section, lining the inlets 254 and extending slightly over the adjacent surface 256. The protective layer may be, for example, silicon dioxide or other material, such as spin-on glass (SOG). This layer protects against potentially damaging etchant (such as TMAH) that is used to form the channel 258 (FIG. 11) from moving through the inlets 254 into and over the control layer 244. In instances where the channel 258 is formed using a dry etch, the layer 280 may not be required.

The protective layer 280 is in place while the channel 258 (or channel 58 of the prior embodiment) is etched. Also in place is another layer 214 that is patterned on the back side of the substrate to define the width of the channel 258. This layer 214 may be formed from a wet- or dry-process silicon dioxide (SiO2), tetraethylorthosilicate ((SiOC2H5)4) (TEOS) based oxides, borophosphosilicate glass (BPSG), phosphosilicate glass (PSG), or borosilicate glass (BSG).

After the channel 258 is etched, the protective layer 280 is removed, thereby to provide fluidic communication from the channel 258, through the inlets 254, and into the chambers 233.

It is contemplated that before the above-mentioned control layers 44, 244 are fabricated on the silicon base 42, 242, the surface of the base that carries the control layer can be etched to define a recess. The recess is filled with polysilicon, the surface of which is made planar (as by chemical-mechanical polishing) with that of the adjacent surface of the base. The polysilicon material underlies the control layer, including the resistive portion, in the space between and surrounding the inlets. The polysilicon makes more durable the portion of the drop generator that spans the channel 58, 258.

Even though the foregoing description has focused on the production of ultra-small droplets suitable for aerosol delivery, it will be appreciated that such small droplets can be generated for other applications. Of course, the drop generators may be used for ejecting ultra-small droplets of ink to enable ink-jet printing with remarkably high resolution. The drop generators of the present invention also could be incorporated with supplies of fluids such as liquids suitable for scent delivery, or dispensing precisely controlled amounts of pesticides, paints, fuels, etc. It is also contemplated that such drop generators may be employed in microfabrication processes like the ones contemplated in this description. For example, ultra-small mandrel-like or other features may be formed using such drop generators to deposit fluidic material to a substrate for further curing or other processing.

Thus, although preferred and alternative embodiments of the present invention have been described, it will be appreciated that the spirit and scope of the invention is not limited to those embodiments, but extend to the various modifications and equivalents as defined in the appended claims.

The invention claimed is:

1. An assembly for producing a drop generator that has a chamber shaped for holding ultra-small volumes of fluid, wherein the drop generator includes an orifice member that substantially covers the chamber and has an orifice therethrough, comprising:
    a substrate;
    a removable mandrel disposed on the substrate and defining the chamber shape, the mandrel being arranged and formed for being covered by the orifice member and thereafter removed; and
    an orifice member that is formed of photopolymer material and that substantially covers the mandrel but for an orifice that extends through the orifice member so that the orifice and the chamber are in fluid communication upon removal of the mandrel, wherein the orifice member material and the mandrel are slow-cross-linking polymers.

2. The assembly of claim 1 wherein the mandrel may be removed by etching.

3. The assembly of claim 1 wherein the mandrel is a photopolymer material.

4. The assembly of claim 3 wherein the photopolymer material includes an optical dye.

5. An assembly for producing a drop generator that has a chamber shaped for holding ultra-small volumes of fluid, wherein the drop generator includes an orifice member that substantially covers the chamber and has an orifice therethrough, comprising:
    a substrate;
    a removable mandrel disposed on the substrate and defining the chamber shape, the mandrel being arranged and formed for being covered by the orifice member and thereafter removed; and
    an orifice member that is formed of photopolymer material and that substantially covers the mandrel but for an orifice that extends through the orifice member so that the orifice and the chamber are in fluid communication upon removal of the mandrel, wherein the mandrel is formed of a relatively slower-cross-linking polymer as compared to the orifice member material.

6. An assembly for producing a plurality of drop generators that each has a chamber shaped for holding ultra-small volumes of fluid, wherein the plurality of drop generators includes a respective plurality of orifice members that substantially covers the respective chamber and has an orifice therethrough, comprising:
    a substrate;
    a plurality of removable mandrels disposed on the substrate and each defining the respective chamber shape, the plurality of removable mandrels being arranged and formed for being covered by the respective plurality of orifice member and each thereafter removed; and
    a plurality of fluid inlets formed in the substrate, each fluid inlet receiving part of a removable mandrel.

7. An assembly for producing a drop generator that has a chamber shaped for holding ultra-small volumes of fluid, wherein the drop generator includes an orifice member that substantially covers the chamber and has an orifice therethrough, comprising:
    a substrate; and
    a removable mandrel disposed on the substrate and defining the chamber shape, the mandrel being arranged and formed for being covered by the orifice member and thereafter removed, wherein the mandrel is selected to be a material such that the orifice member wets the surface of the mandrel that is covered by the orifice member.

8. The assembly of claim 7 wherein the mandrel is formed of spin-on glass material.

9. The assembly of claim 7 wherein the mandrel is metal.

10. The assembly of claim 7 wherein the substrate includes an inlet formed therein and into which inlet extends some of the removable material.

11. A drop generator comprising:
a substrate carrying a transducer;
an orifice member on the substrate and shaped to define a chamber therebetween, adjacent to which chamber resides the transducer, the orifice member including an orifice that opens to the chamber, the chamber having a volume of less than 100 femtoliters.

12. The drop generator of claim 11, wherein the chamber volume is about 25 femtoliters.

13. The drop generator of claim 11 wherein the orifice member includes a plurality of orifices opening to the chamber.

14. A drop generator comprising:
a substrate carrying a transducer;
an orifice member on the substrate and shaped to define a chamber that is adjacent to the transducer, the orifice member including an orifice that opens to the chamber, the chamber having a volume of less than 100 femtoliters; and
the orifice and chamber being defined by a wall that has a constant slope.

15. A drop generator head comprising:
a substrate that carries an array of transducers thereon;
an orifice member shaped to include an array of chambers, each chamber associated with a transducer, the chambers being in fluid communication with one another, and wherein each of the chambers has a volume of less than about 100 femtoliters; and
an array of inlets formed in the substrate for directing liquid to the chambers.

16. A drop generator head comprising:
a substrate that carries an array of transducers thereon;
an orifice member shaped to include an array of chambers, each chamber associated with a transducer, the chambers being in fluid communication with one another;
an array of inlets formed in the substrate for directing liquid to the chambers; and
support islands formed in the orifice member between the chambers and shaped to define fluid paths between chambers.

* * * * *